(12) United States Patent
Becker et al.

(10) Patent No.: US 8,142,384 B2
(45) Date of Patent: Mar. 27, 2012

(54) BLOOD TUBE SYSTEM FOR EXTRACORPOREAL USES, SUCH AS DIALYSIS DEVICES

(76) Inventors: Franz Ferdinand Becker, Rodgau (DE);
Thomas Ryzlewicz, Höslwang (DE);
Reinhold H. Herbst, Possendorf (DE)

(*) Notice: Subject to any disclaimer, the term of this patent is extended or adjusted under 35 U.S.C. 154(b) by 472 days.

(21) Appl. No.: 12/183,877

(22) Filed: Jul. 31, 2008

(65) Prior Publication Data
US 2009/0036816 A1    Feb. 5, 2009

(30) Foreign Application Priority Data

Aug. 1, 2007  (DE) .................. 10 2007 036 125

(51) Int. Cl.
*A61M 37/00* (2006.01)
*A61B 19/00* (2006.01)

(52) U.S. Cl. ........ 604/6.15; 604/403; 604/408; 604/410

(58) Field of Classification Search ............... 604/6.15, 604/6.16, 403, 408, 410
See application file for complete search history.

(56) References Cited

U.S. PATENT DOCUMENTS

| | | | | |
|---|---|---|---|---|
| 3,985,135 | A | * | 10/1976 | Carpenter et al. ............ 604/410 |
| 4,464,172 | A | | 8/1984 | Lichtenstein |
| 5,431,496 | A | * | 7/1995 | Balteau et al. .................. 383/38 |
| 5,824,212 | A | | 10/1998 | Brockhoff |
| 6,773,426 | B2 | * | 8/2004 | Tamari ........................ 604/406 |

FOREIGN PATENT DOCUMENTS

| | | |
|---|---|---|
| DE | 20213693 U1 | 12/2002 |
| DE | 102005001779 A1 | 9/2006 |
| DE | 102005058012 A1 | 6/2007 |
| JP | 04061866 | 2/1992 |

* cited by examiner

*Primary Examiner* — Leslie Deak
(74) *Attorney, Agent, or Firm* — Greer, Burns & Crain, Ltd

(57) ABSTRACT

A blood tube system for extracorporeal uses, such as dialysis devices, wherein an arterial expansion chamber including a lower region for receiving blood, in which a blood inlet channel terminates, and from which a blood outlet channel extends, and an upper region for receiving air, where a venting channel provided with a venting valve extends from the upper region. The blood tube system includes a central region of the expansion chamber which has considerably reduced cross-sectional dimensions, the blood level being adjustable by means of the venting valve in such a manner that blood/air contact takes place in the central region. The amounts of heparin and EPO needed for a dialysis treatment can thereby be reduced.

20 Claims, 2 Drawing Sheets

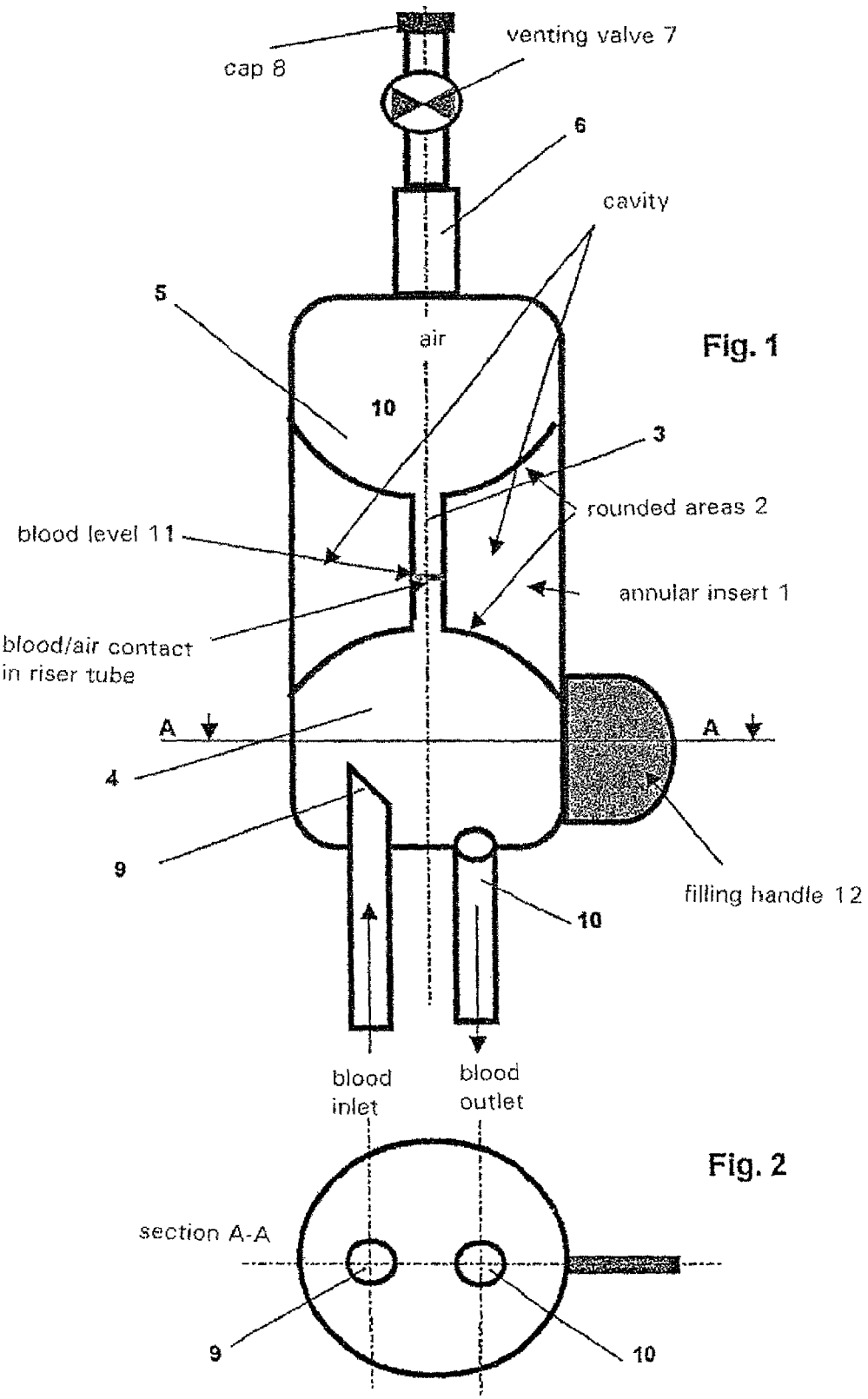

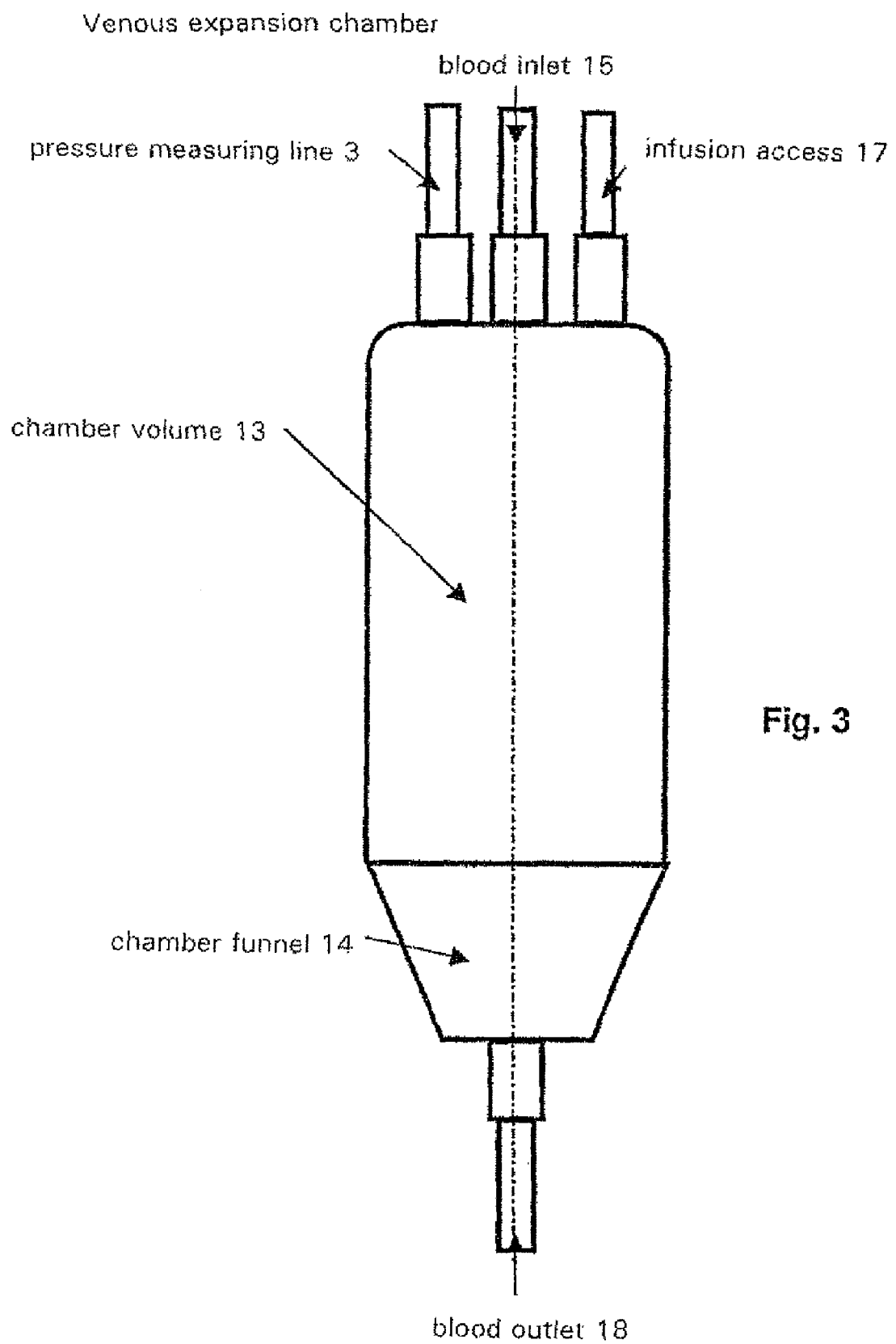

BLOOD TUBE SYSTEM FOR EXTRACORPOREAL USES, SUCH AS DIALYSIS DEVICES

FIELD OF THE INVENTION

The present invention relates to a blood tube system for extracorporeal uses, such as dialysis devices.

BACKGROUND

Considerable amounts of heparin have so far been used in dialysis treatments in which EPO is also administered in great quantities to prevent thrombosis. These substances can be harmful to a patient's health in the long run and also entail considerable costs.

SUMMARY

It is the object of the present invention to describe a solution in which the required amounts of heparin and EPO can be reduced.

The invention will now be described by way of example in connection with its use with a blood tube system for dialysis devices.

According to the invention the blood tube system comprises an arterial expansion chamber which has a lower region used for receiving blood, in which a blood inlet channel terminates and from which a blood outlet channel extends, and which has an upper region for receiving air, wherein a venting channel provided with a venting valve extends from the upper region. According to the invention the expansion chamber has a central, substantially tubular region of considerably reduced cross-sectional dimensions, and the blood level is set by the venting valve in the arterial expansion chamber during treatment in such a manner that blood/air contact takes place in this central constricted region. Preferably, the central region has the shape of a cylindrical tube with a circular or oval cross-section and could be called "riser tube". The constricted region, however, may for example extend in vertical direction in a slightly conical manner. The diameter of this substantially tubular region may approximately equal the diameter of the blood inlet channel and the blood outlet channel without the invention being limited to such a configuration.

During the filling process blood is flowing through a supply nozzle, which preferably projects through the bottom of the expansion chamber into the interior of the lower region of the expansion chamber, into the expansion chamber, and here the venting valve sets the blood level such that it is approximately positioned in the middle of the riser tube. During dialysis the blood level will move upwards and downwards in the riser tube due to a pulsating pump of the blood tube system, the riser tube (or in general words, the central constricted region) having such a length that the blood level remains in the region of the riser tube. An exact setting is carried out at the beginning of a treatment by opening the venting valve.

The length of the riser tube and its diameter depend on the respective blood tube system and dialysis device and can be determined in experimental tests. In a preferred embodiment the cross-sectional area of the central, substantially tubular region is about 1/7 of the cross-sectional area of the lower region of the expansion chamber.

A small blood/air contact area is created by virtue of the configuration according to the invention, whereby the thrombosing risk is considerably reduced. It has been found that, when such an expansion chamber is used, the consumption of heparin and EPO and of other substances can be reduced significantly per person and treatment.

The lower region of the expansion chamber passes with a curved shape, preferably in the form of a conical section, into the riser tube, whereby blood is swirled in the lower region of the expansion chamber. This is intensified by the measure that blood inflow preferably takes place near the edge of the lower region.

According to a preferred embodiment the central constricted region of the expansion chamber is defined by an annular insert fixed in the expansion chamber at a suitable height. Like the expansion chamber proper, said annular insert can be made of plastics. Advantageously, the expansion chamber has the form of a cylinder with rounded edges at the place where upper wall and lower wall pass into the circumferential wall. Preferably, the cylindrical expansion chamber has an oval or circular cross-sectional form.

It is further suggested with advantage that the annular insert is provided at its upper side and at its lower side with concavely shaped wall surfaces, the center of which has positioned therein the passage channel shaped in the form of a riser tube. Advantageously, the annular insert is a hollow body which is circumferential wall is fixed to the inner wall of the expansion chamber in an appropriate way, for instance with the help of an adhesive or by thermowelding.

According to a further proposal of the invention the expansion chamber may be provided with a lateral filling handle which is expediently molded or attached onto the chamber in the lower region. With this filling handle it is possible to slightly tilt the arterial expansion chamber during filling, whereby the filling process is made easier. Moreover, the filling handle can be helpful in aligning the expansion chamber in a defined position in a holder provided to this end. This is also of help to the user.

According to a further proposal of the invention the blood tube system may also comprise a venous expansion chamber, preferably of plastics, which, like the arterial expansion chamber, is in the overpressure region where air is prevented from entering from the environment. According to the invention the venous expansion chamber comprises a cylindrical upper region with a chamber volume reduced to about two thirds of a conventional venous expansion chamber, and a conical lower region from which the blood outlet channel extends. The venous expansion chamber is completely filled with blood by means of a blood inlet channel, and the pressure is measured via a pressure measuring line that is also arranged on the upper side of the venous expansion chamber. This pressure measuring line has a length of at least 60 millimeters, whereby blood is prevented from passing to the pressure connector. Moreover, the venous expansion chamber is provided at the upper side with an infusion access through which the necessary infusions can be supplied. In the lower chamber funnel, the thrombosing sieve found in conventional expansion chambers can be omitted, whereby the amount of heparin needed during an extracorporeal blood treatment can also be reduced considerably.

BRIEF DESCRIPTION OF THE FIGURES

FIG. 1 shows an embodiment of an arterial expansion chamber according to the invention;

FIG. 2 is a section A-A taken through the arterial expansion chamber according to FIG. 1; and FIG. 3 shows an embodiment of a venous expansion chamber according to the invention.

DETAILED DESCRIPTION OF THE INVENTION

The arterial expansion chamber has a cylindrical form with an oval cross-section, wherein an annular insert 1 is inserted into the arterial expansion chamber. This annular insert is provided at the top and at the bottom with concavely rounded areas 2, which terminate in a central channel 3 shaped in the manner of a riser tube.

The channel 3 in the form of a riser tube connects a lower region 4 of the expansion chamber, which is filled with blood, to an upper region 6, which is filled with air. A venting channel 6 which is provided with a venting valve 7 and is closable at its upper side by means of a removable cap 8 extends from the upper region 5.

A blood inlet nozzle 9 which projects into the lower region 4 and through which blood enters into the arterial expansion chamber (the blood will flow off again through a blood outlet channel 10) passes through the bottom of the expansion chamber. The blood outlet channel 10 does not project into the interior of the lower region 4. During the filling process blood flows into the expansion chamber through the longer supply nozzle 9 provided with a bevel, and the blood level 11 is set within the expansion chamber, by opening the venting valve 7 (after cap 8 has been removed), in such a manner that it is located approximately around the middle height of the riser tube 3. The riser tube 3 is of such a length that the blood level 11 will always remain in the area of the riser tube 3 during its pulsating upward and downward movement. This has the consequence that the contact area between blood and air, which prevails in the upper region 5 of the expansion chamber, is minimized.

A filling handle 12 which facilitates the filling process and makes it possible to insert the expansion chamber in a defined position into a holder (not shown in the drawing) is attached to the side of the expansion chamber.

FIG. 2 shows a venous expansion chamber which contains an upper cylindrical chamber 13 of a volume reduced in comparison with conventional venous expansion chambers, and a lower chamber funnel 14. The venous expansion chamber is completely filled with blood by means of a blood inlet channel 15, the blood pressure being here measurable by way of an upper pressure measuring line 16.

Moreover, an infusion access 17 passes through the upper wall of the venous expansion chamber.

A blood outlet channel 18 extends from the bottom of the chamber funnel 14, said blood outlet channel 18 being in alignment with the blood inlet channel 15.

The thrombosing sieve that has so far been used can be omitted in the chamber funnel 14, whereby the amount of heparin needed during dialysis treatment can be reduced.

The invention claimed is:

1. A blood tube system including a pump for use with a dialysis device, comprising:
    an arterial expansion chamber in the system downstream from the pump, the arterial expansion chamber including a lower region for receiving blood, in which a blood inlet channel terminates and from which a blood outlet channel exits, further an upper region for receiving air, a venting channel provided with an adjustable venting valve to selectively open or close extending from the upper region;
    wherein a substantially tubular region of the expansion chamber is formed, which in comparison with the adjoining upper and lower regions of the expansion chamber has reduced cross-sectional dimensions; and
    wherein the blood level is adjustable by way of the adjustable venting valve in its height in such a manner that blood/air contact during dialysis takes place in the central tubular region.

2. The blood tube system of claim 1, wherein the tubular region has the form of a cylindrical riser tube.

3. The blood tube system according to claim 2, and further wherein the tubular region is defined by an annular insert which is fixed in the expansion chamber.

4. The blood tube system according to claim 3, wherein the annular insert is provided at its upper side and at its lower side with concavely shaped wall surfaces.

5. The blood tube system of claim 4, wherein the expansion chamber is provided with a lateral filling handle.

6. The blood tube system of claim 3, wherein the expansion chamber is provided with a lateral filling handle.

7. The blood tube system of claim 2, wherein the blood inlet channel projects with a supply nozzle from underneath through the bottom of the expansion chamber into the interior of the lower region of the expansion chamber.

8. The blood tube system of claim 2, wherein the expansion chamber is provided with a lateral filling handle.

9. The blood tube system of claim 1, wherein the blood inlet channel projects with a supply nozzle from underneath through the bottom of the expansion chamber into the interior of the lower region of the expansion chamber.

10. The blood tube system of claim 9, wherein the end of the supply nozzle is beveled.

11. The blood tube system of claim 9, wherein the expansion chamber is provided with a lateral filling handle.

12. The blood tube system of claim 1, wherein the expansion chamber is provided with a lateral filling handle.

13. The blood tube system of claim 1, wherein the tubular region is located at a vertically central region of the arterial expansion chamber.

14. A blood tube system for extracorporeal uses, such as dialysis devices, comprising:
    an arterial expansion chamber including a lower region for receiving blood, in which a blood inlet channel terminates and from which a blood outlet channel exits, further an upper region for receiving air, a venting channel provided with a venting valve extending from the upper region;
    wherein a vertically central, substantially tubular region of the expansion chamber is formed, which in comparison with the adjoining upper and lower regions of the expansion chamber has reduced cross-sectional dimensions;
    wherein the blood level is adjustable by way of the venting valve in its height in such a manner that blood/air contact during dialysis takes place in the central tubular region, and
    wherein the central region is defined by an annular insert which is fixed in the expansion chamber.

15. The blood tube system of claim 14, wherein the annular insert is provided at its upper side and at its lower side with concavely shaped wall surfaces.

16. The blood tube system of claim 15, wherein the blood inlet channel projects with a supply nozzle from underneath through the bottom of the expansion chamber into the interior of the lower region of the expansion chamber.

17. The blood tube system of claim 15, wherein the expansion chamber is provided with a lateral filling handle.

18. The blood tube system of claim 14, wherein the blood inlet channel projects with a supply nozzle from underneath through the bottom of the expansion chamber into the interior of the lower region of the expansion chamber.

19. The blood tube system of claim 14, wherein the expansion chamber is provided with a lateral filling handle.

20. A blood tube system including a pump for use with a dialysis device, comprising:
    an arterial expansion chamber in the system downstream from the pump, the arterial expansion chamber including a lower region for receiving blood, in which a blood inlet channel terminates and from which a blood outlet channel exits, further an upper region for receiving air, a venting channel provided with an adjustable venting valve to selectively open or close extending from the upper region;

wherein a substantially tubular region of the expansion chamber is formed, which in comparison with the adjoining upper and lower regions of the expansion chamber has reduced cross-sectional dimensions;

wherein the blood level is adjustable by way of the adjustable venting valve in its height in such a manner that blood/air contact during dialysis takes place in the central tubular region; and a venous expansion chamber which comprises a cylindrical upper region, in which a blood inlet channel terminates, and a conical lower region, from which the blood outlet channel extends.

* * * * *